(12) United States Patent
Vermeiren et al.

(10) Patent No.: US 12,207,054 B2
(45) Date of Patent: Jan. 21, 2025

(54) IMPLANTABLE TRANSDUCER WITH INTEGRATED DIAPHRAGM

(71) Applicant: Cochlear Limited, Macquarie University (AU)

(72) Inventors: Jan Vermeiren, Macquarie University (AU); Koen Erik Van den Heuvel, Macquarie University (AU); Rishubh Verma, Macquarie University (AU); Antonin Rambault, Macquarie University (AU)

(73) Assignee: Cochlear Limited, Macquarie University (AU)

(*) Notice: Subject to any disclaimer, the term of this patent is extended or adjusted under 35 U.S.C. 154(b) by 996 days.

(21) Appl. No.: 17/257,832

(22) PCT Filed: Oct. 22, 2019

(86) PCT No.: PCT/IB2019/059026
§ 371 (c)(1),
(2) Date: Jan. 4, 2021

(87) PCT Pub. No.: WO2020/084494
PCT Pub. Date: Apr. 30, 2020

(65) Prior Publication Data
US 2021/0297795 A1  Sep. 23, 2021

Related U.S. Application Data

(60) Provisional application No. 62/749,810, filed on Oct. 24, 2018.

(51) Int. Cl.
*H04R 25/00* (2006.01)
*A61N 1/36* (2006.01)
*A61N 1/375* (2006.01)

(52) U.S. Cl.
CPC ....... *H04R 25/606* (2013.01); *A61N 1/36038* (2017.08); *A61N 1/3754* (2013.01); *H04R 25/65* (2013.01); *H04R 2225/67* (2013.01)

(58) Field of Classification Search
None
See application file for complete search history.

(56) References Cited

U.S. PATENT DOCUMENTS 6,221,024 B1  4/2001  Miesel
6,422,991 B1 * 7/2002  Jaeger .................. H04R 25/606
                                                          600/25

(Continued)

FOREIGN PATENT DOCUMENTS

EP           1596629 A2 * 11/2005 ........... H04R 19/016
KR    10-2006-0099627      9/2006
WO    WO-2016062324 A1 *  4/2016 ............. H04R 1/023

OTHER PUBLICATIONS

International Search Report and Written Opinion dated Jan. 29, 2020 in International Application No. PCT/IB2019/059026.

*Primary Examiner* — Thaddeus B Cox
(74) *Attorney, Agent, or Firm* — Knobbe, Martens, Olson & Bear, LLP (57) ABSTRACT

An apparatus is provided which includes a biocompatible housing configured to be implanted within a recipient. The housing includes a unitary wall including a first wall portion and a second wall portion surrounding a perimeter of the first wall portion. The first wall portion is sufficiently flexible to transmit vibrations between an outer region outside the housing and an inner region within the housing.

20 Claims, 7 Drawing Sheets

(56) References Cited

U.S. PATENT DOCUMENTS

| | | |
|---|---|---|
| 6,465,935 B1 | 10/2002 | Wannke et al. |
| 7,322,930 B2 | 1/2008 | Jaeger |
| 9,533,143 B2 | 1/2017 | Heuvel |
| 2007/0003081 A1* | 1/2007 | Ram .................... H04R 19/016 |
| | | 381/191 |
| 2010/0042184 A1* | 2/2010 | Daglow .................... A61F 2/18 |
| | | 607/57 |
| 2012/0215055 A1 | 8/2012 | Van Vlem et al. |
| 2013/0116497 A1 | 5/2013 | Vermeiren et al. |
| 2013/0190552 A1* | 7/2013 | Leblans ............... H04R 25/606 |
| | | 600/25 |
| 2016/0082249 A1 | 3/2016 | Thenuwara et al. |
| 2018/0221642 A1 | 8/2018 | Blanchard et al. |
| 2019/0054304 A1* | 2/2019 | Maile .................... A61B 5/363 |

* cited by examiner

IMPLANTABLE TRANSDUCER WITH INTEGRATED DIAPHRAGM

BACKGROUND

Field

The present application relates generally to implantable auditory prostheses, and more specifically to implantable transducers for auditory prostheses.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. Auditory prostheses of various types are widely used to improve the lives of users. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Forms of these auditory prostheses which are "mostly implantable," "fully implantable," or "totally implantable" have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs"), mostly implantable cochlear implants ("MICI"), and fully implantable middle ear implants utilizing totally implantable acoustic ("TIA") systems.

While conventional auditory prostheses use externally disposed microphone assemblies, certain mostly, fully, or totally implantable auditory prostheses use subcutaneously implantable microphone assemblies. Such microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region).

SUMMARY

In one aspect disclosed herein, an apparatus is provided which comprises a biocompatible housing configured to be implanted within a recipient. The housing comprises a unitary wall comprising a first wall portion and a second wall portion surrounding a perimeter of the first wall portion. The first wall portion is sufficiently flexible to transmit vibrations between an outer region outside the housing and an inner region within the housing.

In another aspect disclosed herein, a method is provided which comprises providing at least a portion of a biocompatible housing configured to be implanted within a recipient, the portion comprising a wall. The method further comprises, while a first portion of the wall is mechanically coupled to a second portion of the wall, integrally forming a diaphragm on the wall by thinning the first portion of the wall to have a first thickness less than a second thickness of the second portion of the wall.

In another aspect disclosed herein, a hermetic enclosure is provided which comprises a biocompatible chassis comprising at least one opening and a unitary diaphragm configured to transmit vibrations across the biocompatible chassis by deflecting relative to other portions of the biocompatible chassis. The hermetic enclosure further comprises at least one feedthrough that hermetically seals a first opening of the at least one opening. In certain embodiments, the at least one opening further comprises a second opening, and the hermetic enclosure further comprises a biocompatible lid that hermetically seals the second opening. In certain such embodiments, the biocompatible lid and the biocompatible chassis are made from the same material, and the hermetic enclosure further comprises a hermetic seal (e.g., weld) that mechanically couples the biocompatible lid to the biocompatible chassis. In certain embodiments, the vibrations transmitted across the biocompatible chassis to or from an auditory component of the recipient.

BRIEF DESCRIPTION OF THE DRAWINGS

Embodiments are described herein in conjunction with the accompanying drawings, in which.

DETAILED DESCRIPTION

Certain embodiments described herein provide an implantable transducer assembly (e.g., an implantable assembly comprising at least one microphone; an implantable middle ear assembly comprising at least one actuator; an implantable assembly comprising both at least one microphone and at least one actuator) that includes a diaphragm on a wall of the hermetically sealed assembly without a joint seam (e.g., laser weld) in proximity to (e.g., in contact with) the diaphragm that would otherwise adversely affect the performance or vibrational characteristics of the diaphragm. In addition, the absence of such a joint seam advantageously avoids fabrication problems associated with attaching a fragile diaphragm to the wall of the assembly and with undesirable leakage through the joint seam. The diaphragm of certain embodiments is fabricated by micromachining (e.g., laser micromachining) a wall of the assembly to reduce a thickness of at least a portion of the wall, thereby forming a unitary wall that comprises the diaphragm (e.g., the diaphragm is integral and/or monolithic with other wall portions surrounding the diaphragm).

The teachings detailed herein are applicable, in at least some embodiments, to any type of auditory prosthesis utilizing an implantable transducer assembly including but not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Embodiments can include any type of auditory prosthesis that can utilize the teachings detailed herein and/or variations thereof. Certain such embodiments can be referred to as "partially implantable," "semi-implantable," "mostly implantable," "fully implantable," or "totally implantable" auditory prostheses. In some embodiments, the teachings detailed herein and/or variations thereof can be utilized in other types of prostheses beyond auditory prostheses.

Figure 1:
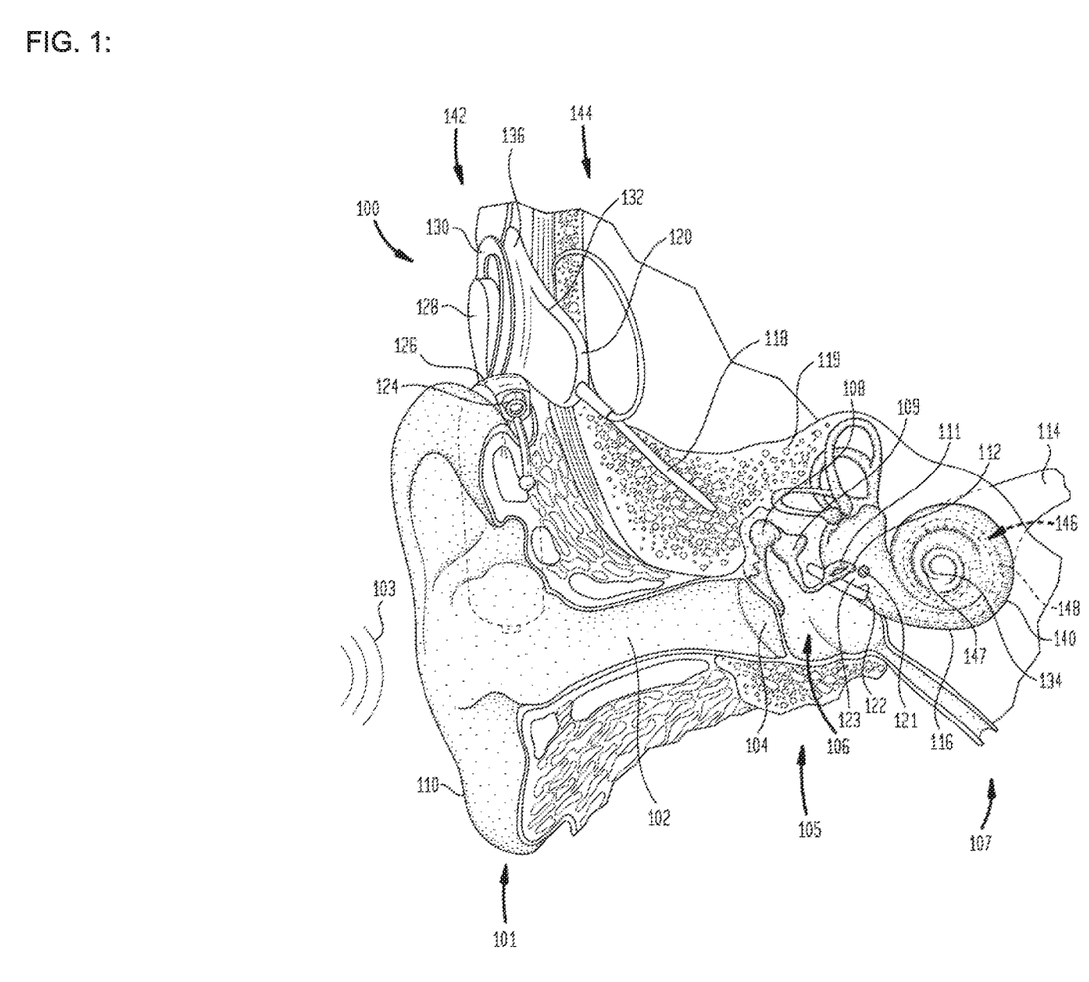
FIG. 1 is a perspective view of an example cochlear implant auditory prosthesis implanted in a recipient in accordance with certain embodiments described herein.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and a microphone assembly 124 that is external to the recipient (e.g., a partially implantable cochlear implant). An example auditory prosthesis 100 (e.g., a totally implantable cochlear implant; a mostly implantable cochlear implant) in accordance with certain embodiments described herein can replace the external microphone assembly 124 shown in FIG. 1 with a subcutaneously implantable microphone assembly 124, as described more fully herein.

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 processes the output of the microphone 124 and generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other embodiments, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Figure 2:
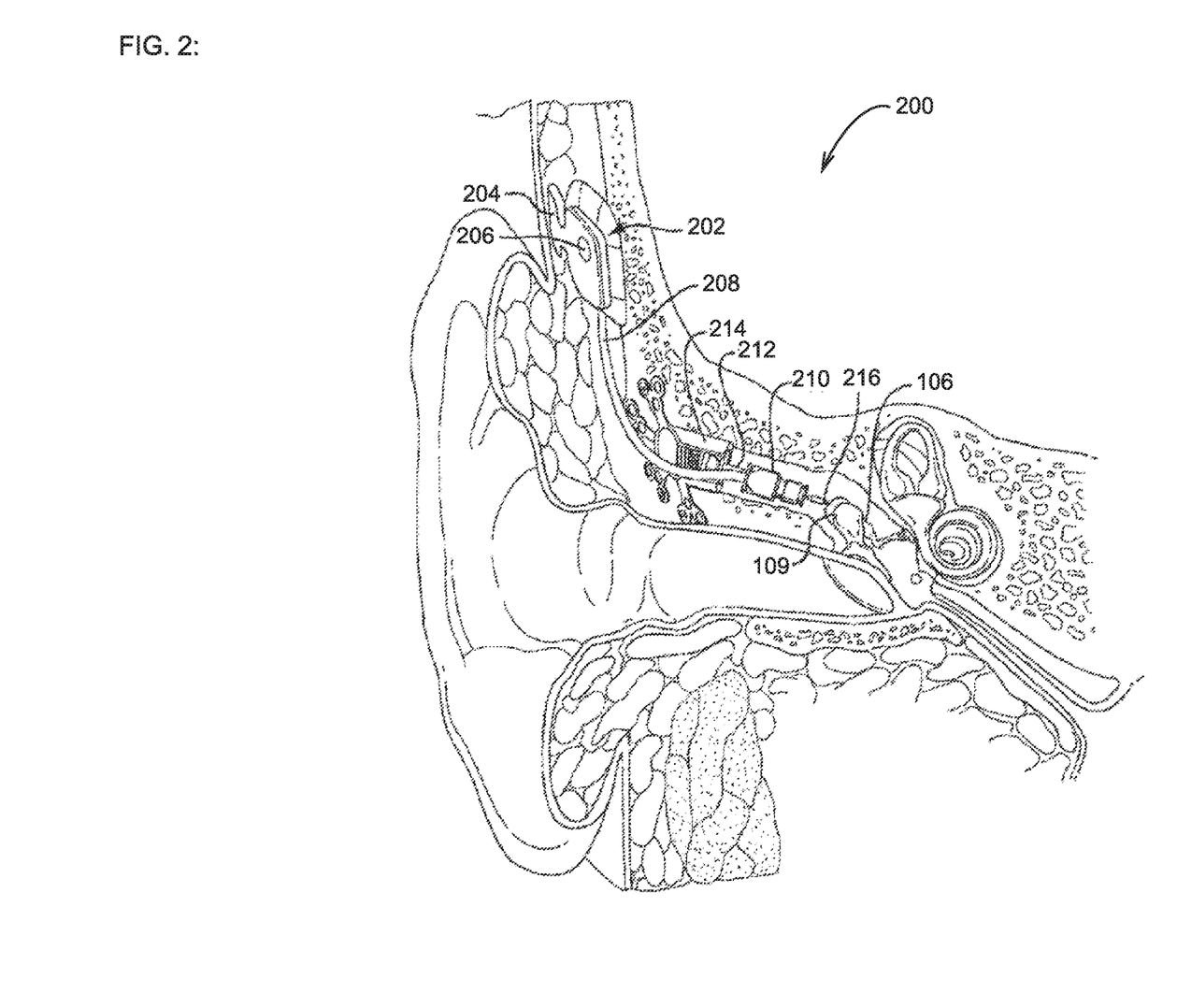
FIG. 2 is a perspective view of an example fully implantable middle ear implant auditory prosthesis implanted in a recipient in accordance with certain embodiments described herein.

FIG. 2 schematically illustrates a perspective view of an example fully implantable auditory prosthesis 200 (e.g., fully implantable middle ear implant or totally implantable acoustic system), implanted in a recipient, utilizing an acoustic actuator in accordance with certain embodiments described herein. The example auditory prosthesis 200 of FIG. 2 comprises a biocompatible implantable assembly 202 (e.g., comprising an implantable capsule) located subcutaneously (e.g., beneath the recipient's skin and on a recipient's skull). While FIG. 2 schematically illustrates an example implantable assembly 202 comprising a microphone, in other example auditory prostheses 200, a pendant microphone can be used (e.g., connected to the implantable assembly 202 by a cable). The implantable assembly 202 includes a signal receiver 204 (e.g., comprising a coil element) and an acoustic transducer 206 (e.g., a microphone comprising a diaphragm and an electret or piezoelectric transducer) that is positioned to receive acoustic signals through the recipient's overlying tissue. The implantable assembly 202 may further be utilized to house a number of components of the fully implantable auditory prosthesis 200. For example, the implantable assembly 202 can include an energy storage device and a signal processor (e.g., a sound processing unit). Various additional processing logic and/or circuitry components can also be included in the implantable assembly 202 as a matter of design choice.

For the example auditory prosthesis 200 shown in FIG. 2, the signal processor of the implantable assembly 202 is in operative communication (e.g., electrically interconnected via a wire 208) with an actuator 210 (e.g., comprising a transducer configured to generate mechanical vibrations in response to electrical signals from the signal processor). In certain embodiments, the example auditory prosthesis 100, 200 shown in FIGS. 1 and 2 can comprise an implantable microphone assembly, such as the microphone assembly 206 shown in FIG. 2. For such an example auditory prosthesis 100, the signal processor of the implantable assembly 202 can be in operative communication (e.g., electrically interconnected via a wire) with the microphone assembly 206 and the stimulator unit of the main implantable component 120. In certain embodiments, at least one of the microphone assembly 206 and the signal processor (e.g., a sound processing unit) is implanted on or within the recipient.

The actuator 210 of the example auditory prosthesis 200 shown in FIG. 2 is supportably connected to a positioning system 212, which in turn, is connected to a bone anchor 214 mounted within the recipient's mastoid process (e.g., via a hole drilled through the skull). The actuator 210 includes a connection apparatus 216 for connecting the actuator 210 to the ossicles 106 of the recipient. In a connected state, the connection apparatus 216 provides a communication path for acoustic stimulation of the ossicles 106 (e.g., through transmission of vibrations from the actuator 210 to the incus 109).

During normal operation, ambient acoustic signals (e.g., ambient sound) impinge on the recipient's tissue and are received transcutaneously at the microphone assembly 206. Upon receipt of the transcutaneous signals, a signal processor within the implantable assembly 202 processes the signals to provide a processed audio drive signal via wire 208 to the actuator 210. As will be appreciated, the signal processor may utilize digital processing techniques to provide frequency shaping, amplification, compression, and other signal conditioning, including conditioning based on recipient-specific fitting parameters. The audio drive signal causes the actuator 210 to transmit vibrations at acoustic frequencies to the connection apparatus 216 to affect the desired sound sensation via mechanical stimulation of the incus 109 of the recipient.

The subcutaneously implantable microphone assembly 202 is configured to respond to auditory signals (e.g., sound; pressure variations in an audible frequency range) by generating output signals (e.g., electrical signals; optical signals; electromagnetic signals) indicative of the auditory signals received by the microphone assembly 202, and these output signals are used by the auditory prosthesis 100, 200 to generate stimulation signals which are provided to the recipient's auditory system. To compensate for the decreased acoustic signal strength reaching the microphone assembly 202 by virtue of being implanted, the diaphragm of an implantable microphone assembly 202 is configured to provide higher sensitivity than are external non-implantable microphone assemblies (e.g., by using diaphragms that are larger than diaphragms for external non-implantable microphone assemblies).

The example auditory prostheses 100 shown in FIG. 1 utilizes an external microphone 124 and the auditory prosthesis 200 shown in FIG. 2 utilizes an implantable microphone assembly 206 comprising a subcutaneously implantable acoustic transducer. In certain embodiments described herein, the auditory prosthesis 100 utilizes one or more implanted microphone assemblies on or within the recipient. In certain embodiments described herein, the auditory prosthesis 200 utilizes one or more microphone assemblies that are positioned external to the recipient and/or that are implanted on or within the recipient, and utilizes one or more acoustic transducers (e.g., actuator 210) that are implanted on or within the recipient. In certain embodiments, an external microphone assembly can be used to supplement an implantable microphone assembly of the auditory prosthesis 100, 200. Thus, the teachings detailed herein and/or variations thereof can be utilized with any type of external or implantable microphone arrangement, and the acoustic transducers shown in FIGS. 1 and 2 are merely illustrative.

Figure 3:
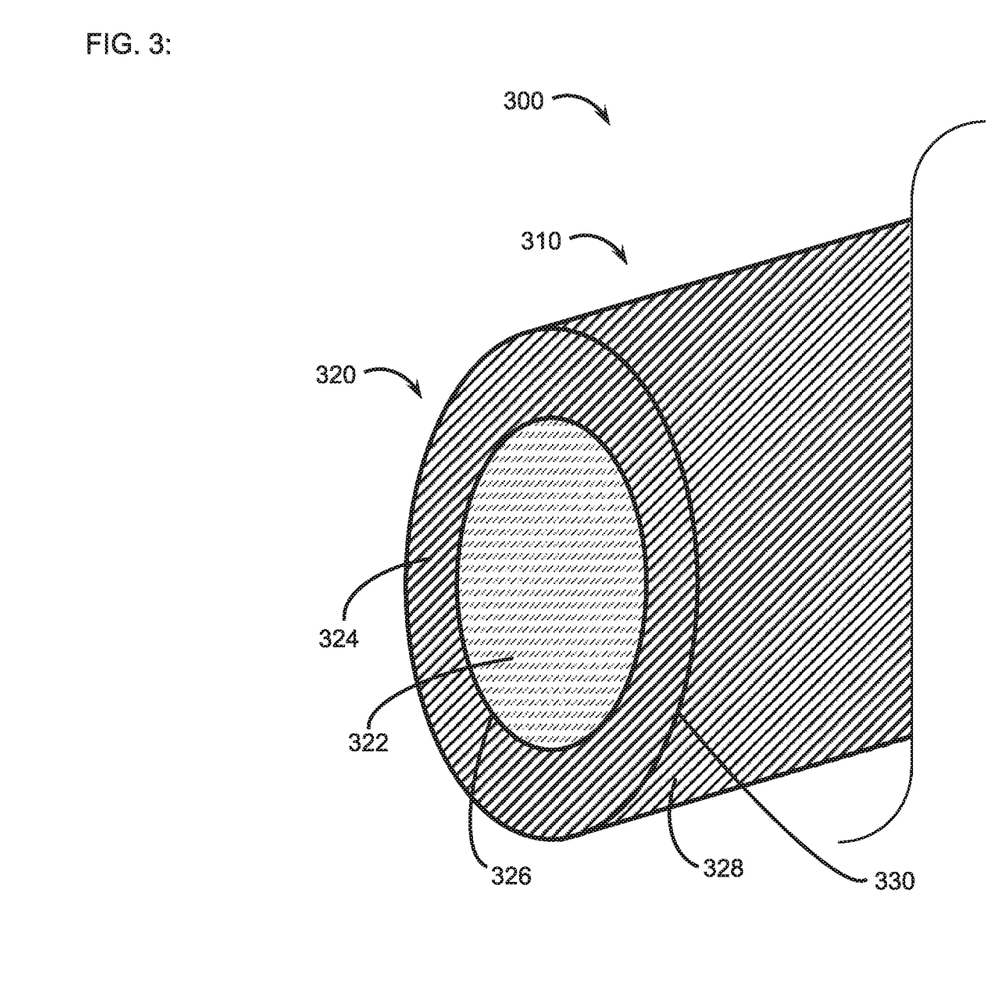
FIG. 3 schematically illustrates an example apparatus in accordance with certain embodiments described herein.

FIG. 3 schematically illustrates an example apparatus 300 in accordance with certain embodiments described herein. The apparatus 300 comprises a biocompatible housing 310 configured to be implanted within a recipient and comprising a unitary wall 320. The unitary wall 320 comprises a first wall portion 322 and a second wall portion 324 surrounding a perimeter 326 of the first wall portion 322. The first wall portion 322 is sufficiently flexible to transmit vibrations between an outer region 311 outside the housing 310 and an inner region 312 within the housing 310.

In certain embodiments, the second wall portion 324 has an inner surface 325 which at least partially bounds the inner region 312 within the housing 310. In certain embodiment, the unitary wall 320 is integral and/or monolithic with another one or more walls or wall portions of the housing 310 (e.g., a third wall portion 328) at a periphery of the housing 310.

In certain embodiments, the apparatus 300 comprises an acoustic transducer configured to be implanted within the recipient and operatively coupled to an auditory prosthesis used by the recipient. For example, the apparatus 300 can comprise a microphone 124 (e.g., subcutaneous microphone or middle ear microphone) or implantable microphone assembly 202 configured to convert received vibrations and/or pressure changes within the recipient's body, based on sound waves incident to the recipient's body, into electrical or optical signals transmitted to other portions of an auditory prosthesis 100, 200 (e.g., as schematically shown in FIGS. 1 and 2). The apparatus 300 of certain such embodiments is configured to detect vibrations and/or pressure changes from at least a partially functional portion of the recipient's auditory system (e.g., middle ear structures and/or cavities; inner ear structures and/or cavities) and to convert the detected vibrations and/or pressure changes into electrical signals. In certain embodiments, the apparatus 300 comprises an acoustic transducer (e.g., microphone) integrated within the housing 310, and the housing 310 is a casing of a cochlear implant auditory prosthesis. For example, the casing of the cochlear implant auditory prosthesis can include the microphone as well as other components of the cochlear implant auditory prosthesis (e.g., stimulation electronics and sound processing electronics), such that the cochlear implant auditory prosthesis is contained in only the single implantable casing (e.g., with the microphone diaphragm formed in the top shells of the cochlear implant casing).

For another example, the apparatus 300 can comprise an implantable actuator 210 configured to be mechanically coupled to a portion of the recipient's auditory system and to generate acoustical vibrations in response to electrical signals received from other portions (e.g., the implantable assembly 202) of the auditory prosthesis 200 with these acoustical vibrations transmitted to the recipient's auditory system (e.g., as schematically shown in FIG. 2). The apparatus 300 of certain such embodiments is configured to receive electrical signals and to generate vibrations and/or pressure changes that are applied to at least a partially functional portion of the recipient's auditory system (e.g., middle ear structures and/or cavities; inner ear structures and/or cavities). In certain embodiments, the apparatus 300 comprises at least one acoustic transducer (e.g., at least one microphone) and at least one actuator integrated within a common implantable housing 310.

In certain embodiments, the housing 310 comprises an enclosure (e.g., casing; chassis; can) comprising a biocompatible material (e.g., titanium; titanium alloy) and is configured to contain one or more transducers (e.g., acoustic transducers; mechanical-electrical transducers) and electronic circuitry (e.g., electronic circuit elements, including but not limited to one or more microprocessors, electrical insulation, electrical shielding, one or more electrical feedthroughs) in the inner region 312 within the housing 310. For example, the housing 310 can bound the inner region 312 within the housing 310 and can hermetically seal the inner region 312 from the outer region 311 outside the housing 310 (e.g., can be substantially impenetrable to air and body fluids).

While FIG. 3 schematically illustrates an example housing 310 that has a substantially tubular shape (e.g., cylindrical with a cylindrical third wall portion 328 with a circular cross-section in a plane perpendicular to a longitudinal axis of the housing 310), the housing 310 can have any shape, including but not limited to: tubular; non-tubular; cylindrical; non-cylindrical; parallelepiped; geometric cross-sectional shapes (e.g., circular; elliptical; rectangular; square; polygonal); irregular cross-sectional shapes. While FIG. 3 schematically illustrates the housing 310 having a corner 330 (e.g., 90 degrees) between an edge of the second wall portion 324 and an edge of the third wall portion 328, in certain other embodiments, the housing 310 has a smooth contour (e.g., no corner) between the second wall portion 324 and the third wall portion 328.

As used herein, the term "unitary" has its broadest reasonable meaning, which includes but is not limited to, forming a single or uniform entity; integral; monolithic. For example, the first wall portion 322 and the second wall portion 324 of the unitary wall 320 can be integral with one another, monolithic with one another, and/or in mechanical communication with one another without a joint seam between the first wall portion 322 and the second wall portion 324. The unitary wall 320 can also be integral and/or monolithic with other walls or other wall portions of the housing 310. For example, as shown in FIG. 3, the unitary wall 320 can be integral and/or monolithic with the third wall portion 328 (e.g., the second wall portion 324 of the unitary wall 320 can be integral with, monolithic with, and/or in mechanical communication with the third wall portion 328 without a joint seam between the second wall portion 324 and the third wall portion 328).

In certain embodiments, the unitary wall 320 of the housing 310 is planar, while in certain other embodiments, the unitary wall 320 is curved (e.g., bowed; concave; convex), and/or can have one or more protrusions or recesses. While FIG. 3 schematically illustrates an example first wall portion 322 that has a circular perimeter 326 and an example second wall portion 324 that has a circular perimeter (e.g., at the corner 330), each of the first wall portion 322 and the second wall portion 324 can have any shape, including but not limited to: geometric (e.g., elliptical, rectangular, square, polygonal); irregular.

In certain embodiments, the first wall portion 322 has a first thickness between an inner side of the first wall portion 322 (e.g., facing the inner region 312 within the housing 310) and an outer side of the first wall portion 322 (e.g., facing the outer region 311 outside the housing 310), and the second wall portion 324 has a second thickness between an inner side of the second wall portion 324 and an outer side of the second wall portion 324. In certain embodiments, the first thickness (e.g., in a range of 10 microns to 100 microns; in a range of 10 microns to 50 microns; in a range of 15 microns to 30 microns; 20 microns; 25 microns) is less than the second thickness (e.g., in a range greater than 100 microns). While the example first wall portion 322 of FIG. 3 is substantially uniform across the area of the first wall portion 322 (e.g., the first wall portion 322 has a uniform thickness across the area of the first wall portion 322), in certain other embodiments, the first wall portion 322 has a non-uniform thickness. In certain embodiments, at least a portion of the first wall portion 322 is configured to flex (e.g., elastically deform) in response to forces applied to the first wall portion 322 (e.g., by vibrations and/or pressure changes applied to either the outer side or the inner side of the first wall portion 322).

In certain embodiments, the inner region 312 within the housing 310 can be configured to contain a transducer (e.g., acoustic transducer; mechanical-electrical transducer; microphone assembly 124, 202; actuator 210) of the apparatus 300 which is in mechanical communication with the first wall portion 322 (e.g., with the housing 310 bounding the inner region 312 and hermetically sealing the inner region 312 from the outer region 311). For example, the electronic circuitry of the transducer can be mechanically coupled to the first wall portion 322 such that vibrations received on a first side of the first wall portion 322 are transmitted to a second side of the first wall portion 322. In certain such embodiments in which the acoustic transducer comprises a microphone (e.g., electret; magnetic; dynamic; piezoelectric; optical; electromechanical), vibrations received at the outer surface of the first wall portion 322 are transmitted to the inner surface of the first wall portion 322 and are converted into electrical signals by the transducer. In certain other such embodiments in which the acoustic transducer comprises an actuator, the transducer generates and applies vibrations to the inner surface of the first wall portion 322, which are transmitted via the outer surface of the first wall portion 322 to a portion of the recipient's auditory system.

Figure 4A:
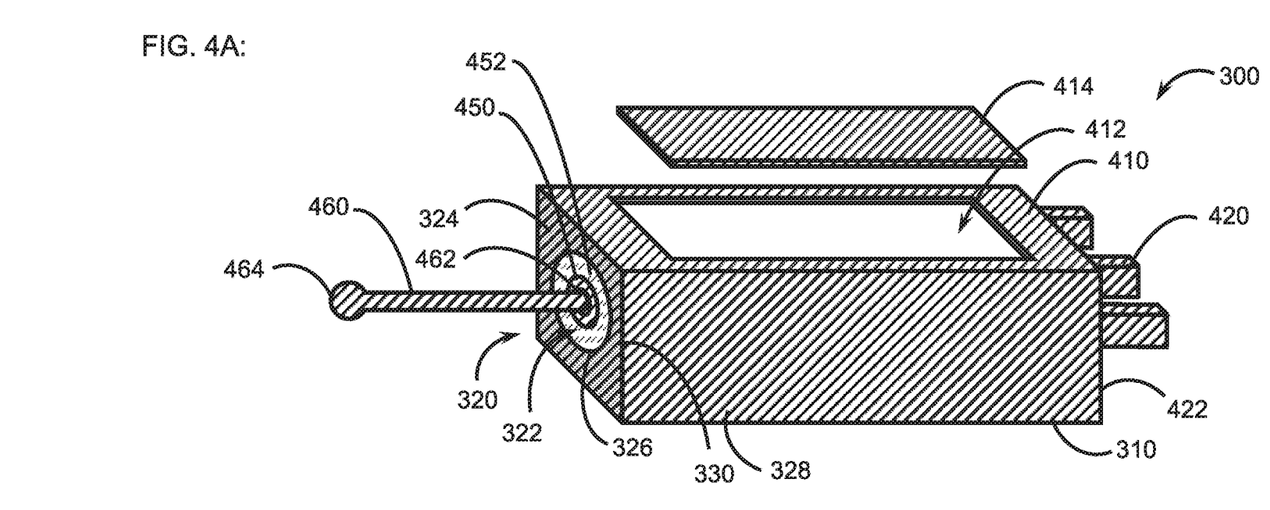
FIGS. 4A-4C schematically illustrate various views of another example apparatus in accordance with certain embodiments described herein.
Figure 4B:
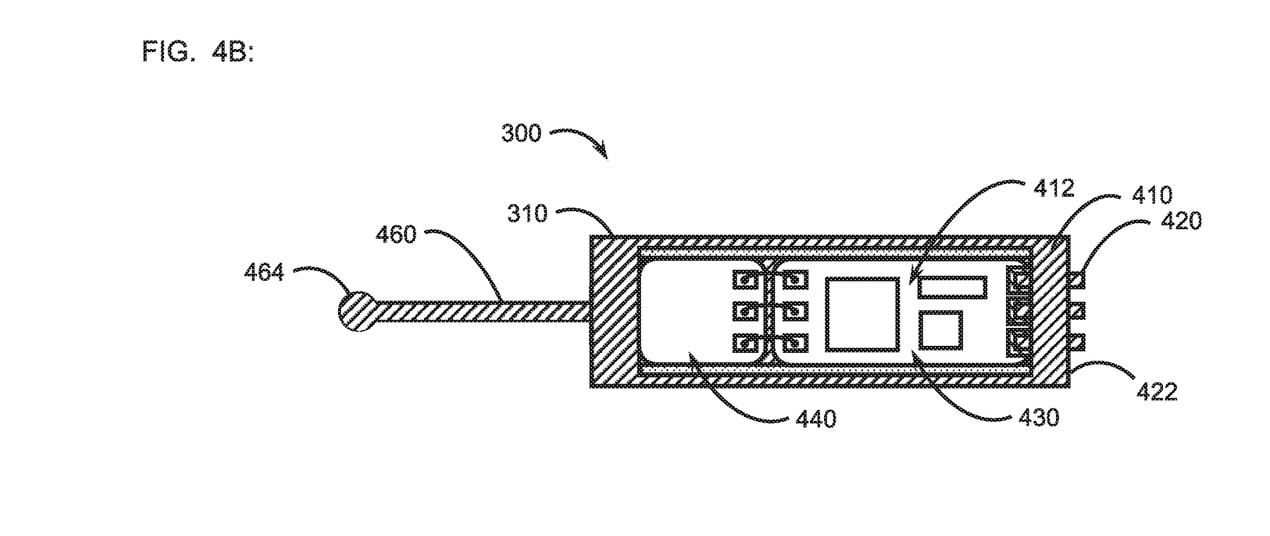
Figure 4C:
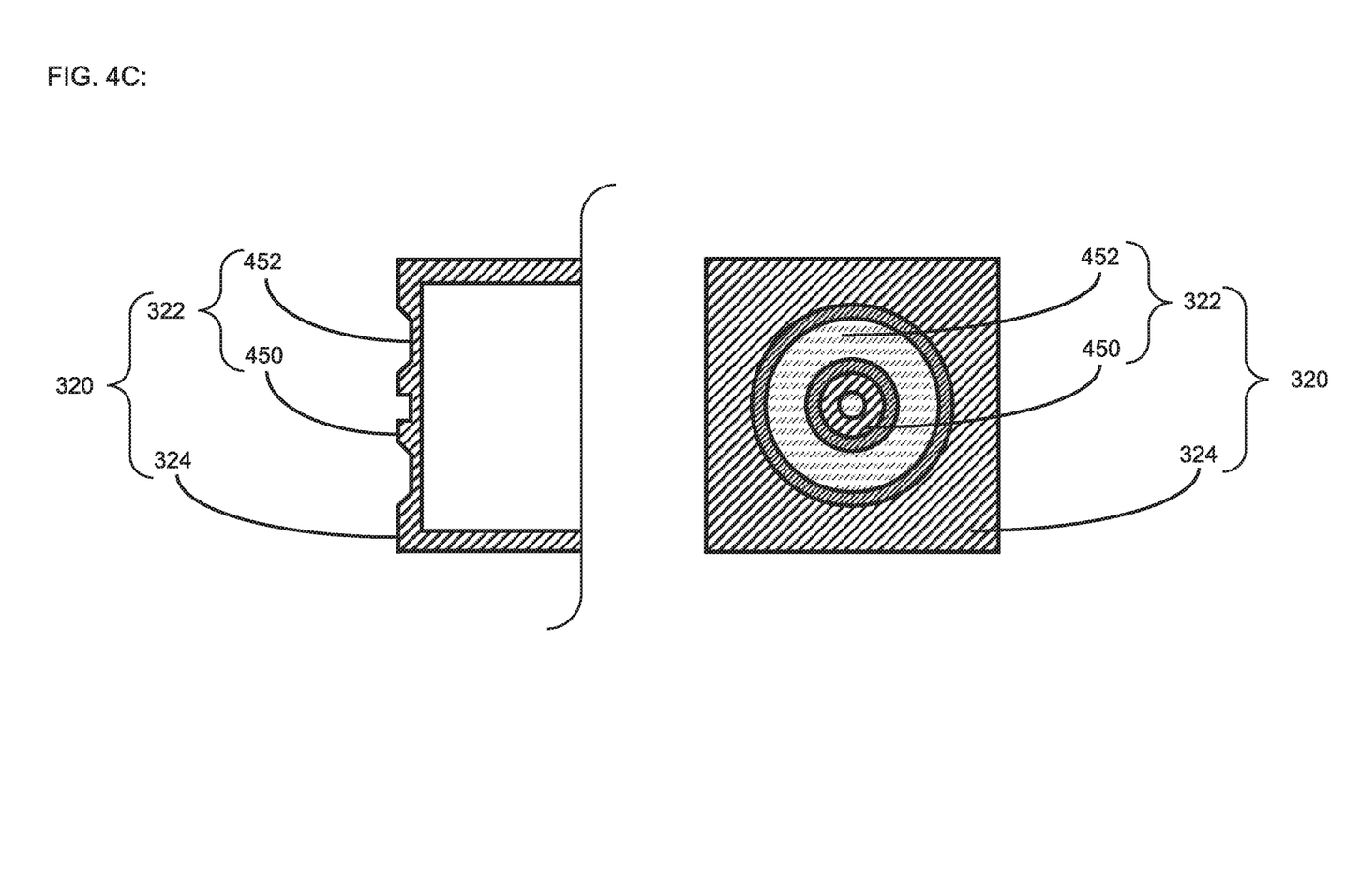

FIGS. 4A-4C schematically illustrate various views of another example apparatus 300 in accordance with certain embodiments described herein. The housing 310 of FIGS. 4A-4C comprises a body 410 having a parallelepiped shape with a length (e.g., in a range of 5 millimeters to 15 millimeters; 9 millimeters), a width (e.g., in a range of 1 millimeter to 6 millimeters; 3.5 millimeters), and a height (e.g., in a range of 1 millimeter to 6 millimeters; 3.5 millimeters). As schematically illustrated in FIGS. 4A-4C, the second wall portion 324 of the unitary wall 320 has a rectangular edge mechanically coupled to an edge of the third wall portion 328, forming the corner 330, and the first wall portion 322 has a circular perimeter 326 surrounded by the second wall portion 324.

The body 410 has at least one opening 412 configured to provide access to the inner region 312 of the housing 310 during assembly of the apparatus 300 (e.g., to allow the electronic circuitry of the transducer to be inserted within the housing 310 and to connect the transducer to the first wall portion 322). In certain embodiments, the at least one opening 412 provides "line-of-sight" access to the inner surface 325 of the second wall portion 324 (e.g., the inner surface 325 of the second wall portion 324 is viewable through the at least one opening 412). The housing 310 further comprises at least one lid 414 configured to be joined (e.g., soldered; brazed; welded; laser welded) to the body 410 (e.g., hermetically sealing the opening 412). The joint seams between the body 410 and the at least one lid 414 are spaced away from the first wall portion 322. FIG. 4A is a perspective view of the example apparatus 300 prior to the at least one lid 414 being joined to the body 410 in accordance with certain embodiments described herein.

In certain embodiments, the housing 310 further comprises at least one electrical feedthrough 420 in electrical communication with the electronic circuitry of the transducer. For example, the at least one electrical feedthrough 420 can extend through and be electrically insulated from a wall 422 of the body 410, spaced away from the first wall portion 322, such that the at least one electrical feedthrough 420 is configured to transmit electrical signals between the inner region 312 within the housing 310 and the outer region 311 outside the housing 310. In certain embodiments, the wall 422 comprises a plate or other structure through which the at least one electrical feedthrough 420 extend, and the wall 422 is configured to be joined (e.g., soldered; brazed; welded; laser welded) to the body 410 to hermetically seal a corresponding opening (not shown) of the body 410 with the at least one electrical feedthrough 420 extending between the inner region 312 and the outer region 311.

FIG. 4B is a top view of the example apparatus 300 of FIG. 4A showing a portion of the inner region 312 through the opening 412 prior to the at least one lid 414 being joined to the body 410 in accordance with certain embodiments described herein. Within the housing 310, the at least one electrical feedthrough 420 is electrically coupled to the electronic circuitry 430, and the electronic circuitry 430 is electrically coupled to the transducer 440 which is mechanically (e.g., pneumatically) coupled to an inner side of the first wall portion 322. For example, the transducer 440 can be acoustically sealed against the inner side of the first wall portion 322 by a sealing element (e.g., epoxy; O-ring; double-sided adhesive tape). In certain embodiments, the apparatus 300 comprises at least one electrically insulating material configured to electrically insulate one or both of the electronic circuitry 430 and the transducer 440 from the body 410 and/or at least one electrically shielding material configured to provide electromagnetic shielding to one or both of the electronic circuitry 430 and the transducer 440.

In certain embodiments in which the apparatus 300 comprises an implantable microphone assembly, electrical signals are generated by the microphone (e.g., the transducer 440 and the circuitry 430) and are transmitted via the at least one electrical feedthrough 420 to other portions of the acoustic prosthesis (e.g., to a stimulator unit 120 of a cochlear implant auditory prosthesis). In certain other embodiments in which the apparatus 300 comprises an actuator (e.g., a portion of a middle ear implant auditory prosthesis), the electrical signals are transmitted via the at least one electrical feedthrough 420 to the electrical circuitry 430 and the transducer 440 within the housing 310 from other portions of the acoustic prosthesis (e.g., from an implantable assembly 202 of a middle ear implant auditory prosthesis) and are used to control the vibrations of the first wall portion 322 to be transmitted to a portion of the recipient's auditory system. Examples of the body 410, at least one electrical feedthrough 420, electronic circuitry 430, and transducer 440 in accordance with certain embodiments described herein are described in U.S. Pat. No. 9,533,143.

FIG. 4C schematically illustrates a cross-sectional view and a front view of the example unitary wall 320 of FIG. 4A in accordance with certain embodiments described herein. As schematically illustrated by FIG. 4C, the inner surface 325 of the second wall portion 324 at least partially bounds the inner region 312 within the housing 310, and the unitary wall 320 is integral and/or monolithic with another one or more walls or wall portions of the housing 310 (e.g., a third wall portion 328) at a periphery of the housing 310.

In certain embodiments, as schematically illustrated by FIGS. 4A and 4C, a central portion 450 of the first wall portion 322 has a third thickness (e.g., in a range greater than 100 microns) that is larger than the first thickness of a peripheral portion 452 of the first wall portion 322, the peripheral portion 452 surrounding the central portion 450. The central portion 450 of certain embodiments is configured to be mechanically coupled to additional components (e.g., an elongate member 460) configured to transmit vibrations between the first wall portion 322 and a predetermined portion of the recipient's auditory system. For example, as schematically illustrated in FIG. 4C, the central portion 450 comprises a recess configured to receive and be mechanically coupled (e.g., by soldering; brazing; welding; laser welding) to the first end portion 462 of the elongate member 460. In certain such embodiments, the peripheral portion 452 of the first wall portion 322 is configured to flex (e.g., elastically deform) in response to forces applied to the first wall portion 322 (e.g., by vibrations and/or pressure changes applied to either the outer side or the inner side of the first wall portion 322) while the central portion 450 is not configured to flex in response to these forces but is configured to move due to the flexing of the peripheral portion 452.

In certain embodiments, the apparatus 300 further comprises an elongate member 460 (e.g., ball wire; rod) in mechanical communication with the first wall portion 322. A first end portion 462 of the elongate member 460 is mechanically coupled to the first wall portion 322 (e.g., to the central portion 450 of the first wall portion 322) and a second end portion 464 of the elongate member 460 is configured to be mechanically coupled to an at least partially functioning portion of the recipient's auditory system. In certain embodiments in which the apparatus 300 comprises an implantable microphone assembly, vibrations from the at least partially functioning portion of the recipient's auditory system (e.g., generated by received sound signals) are transmitted via the elongate member 460 to the first wall portion 322. In certain embodiments in which the apparatus 300 comprises an actuator (e.g., a portion of a middle ear implant auditory prosthesis), vibrations of the first wall portion 322 (e.g., generated by the transducer 440) are transmitted via the elongate member 460 to the at least partially functioning portion of the recipient's auditory system. The elongate member 460 of certain embodiments comprises a biocompatible material (e.g., titanium; titanium alloy; plastic; ceramic; glass), has a length (e.g., in a range of 3 millimeters to 10 millimeters; 6 millimeters), and a width (e.g., in a range of 0.2 millimeter to 1 millimeter; 0.4 millimeter). While FIGS. 4A-4C schematically illustrate the elongate member 460 as being straight with a substantially uniform cross-section in a plane perpendicular to a longitudinal axis of the elongate member 460, in certain other embodiments, the elongate member 460 is at least partially curved and/or has a non-uniform cross-section. Examples of elongate members 460 in accordance with certain embodiments described herein are described in U.S. Pat. Appl. Publ. No. 2013/0116497A1.

Figure 5:
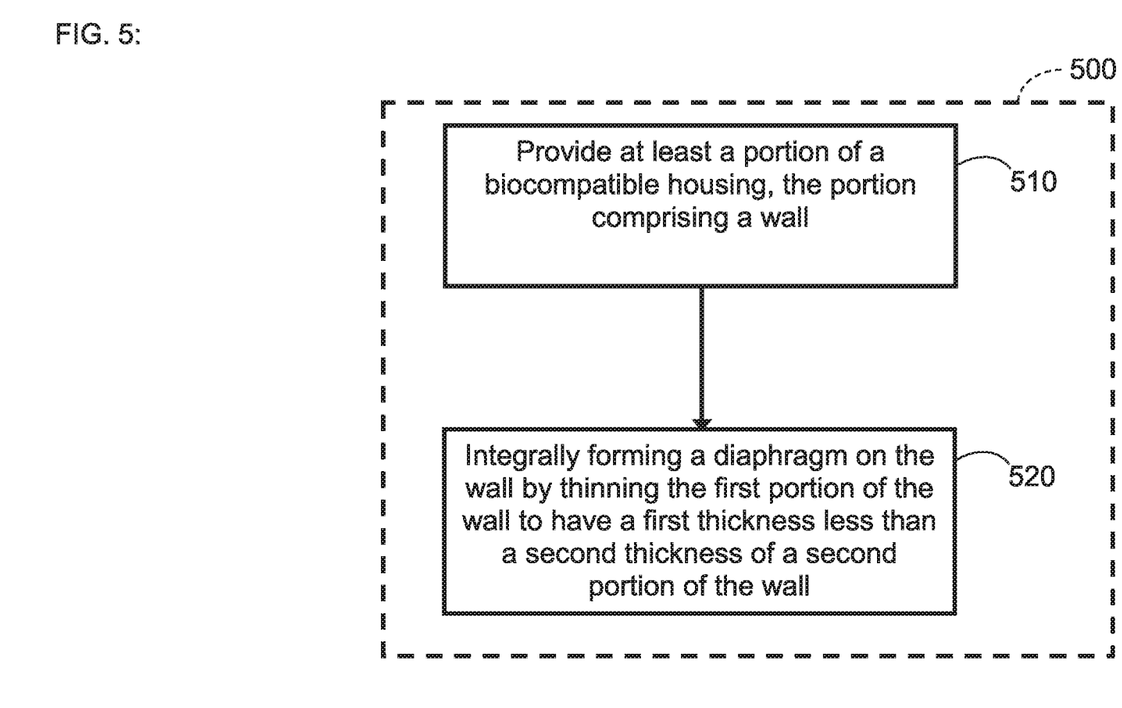
FIG. 5 is a flow diagram of an example method in accordance with certain embodiments described herein.
Figure 6A:
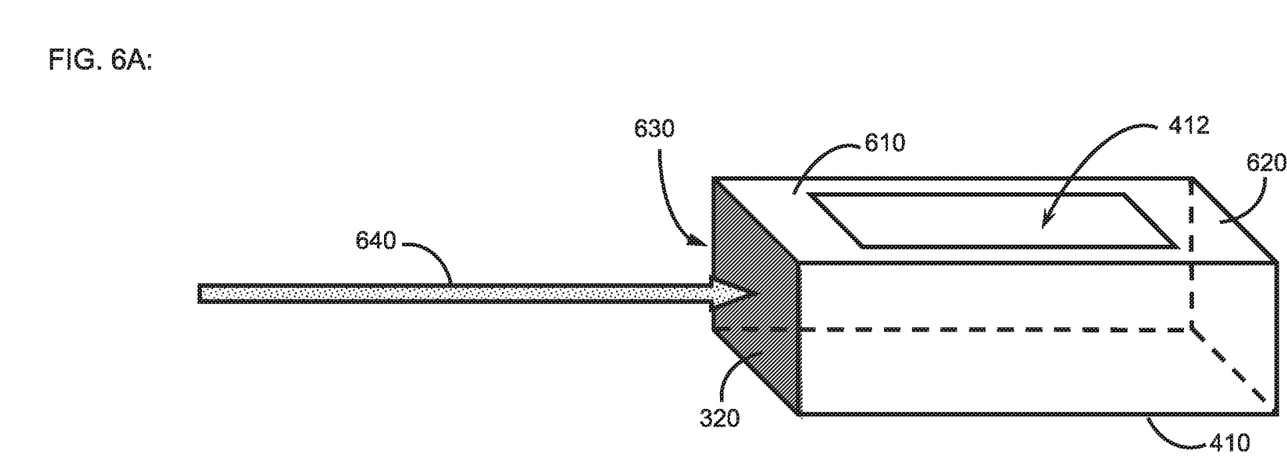
FIGS. 6A and 6B schematically illustrate two example configurations for performing the method of FIG. 5 in accordance with certain embodiments described herein.
Figure 6B:
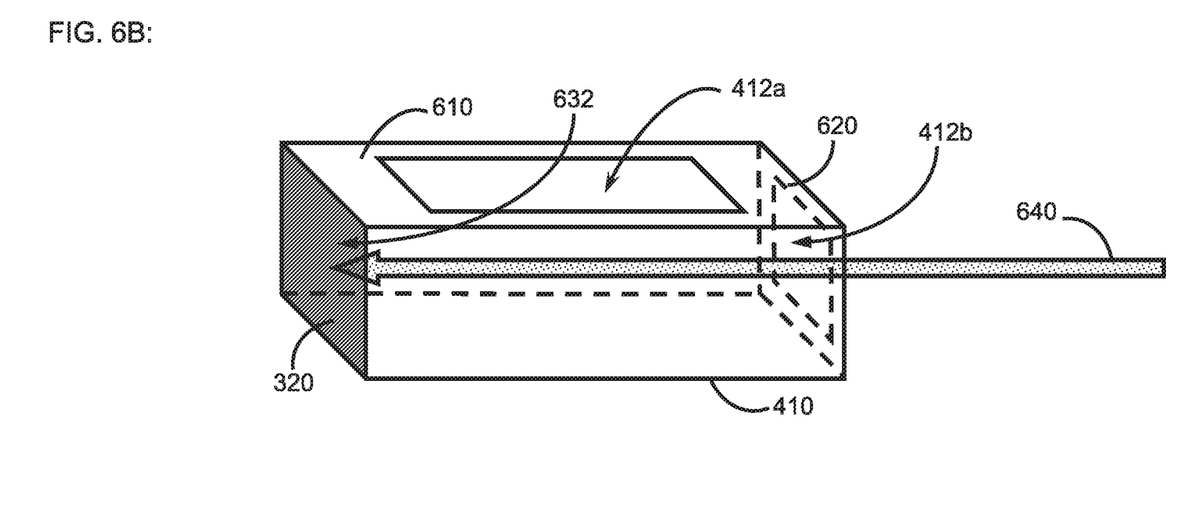

FIG. 5 is a flow diagram of an example method 500 in accordance with certain embodiments described herein. FIGS. 6A and 6B schematically illustrate two example configurations for performing the method 500 in accordance with certain embodiments described herein. While the example method 500 is described herein by referring to the example apparatus 300 of FIGS. 3, 4A-4C, and 6A-6B, other apparatuses are also compatible with the example method 500 in accordance with certain embodiments described herein. For example, the method 500 described herein can be applied to any of a variety of implantable medical devices that utilize a diaphragm formed on a wall of the device.

In an operational block 510, the method 500 comprises providing at least a portion of a biocompatible housing 310 configured to be implanted within a recipient. The portion of the biocompatible housing 310 comprises a wall 320. In an operational block 520, the method 500 further comprises, while a first portion 322 of the wall 320 is mechanically coupled to a second portion 324 of the wall 320, integrally forming a diaphragm on the wall 320 by thinning the first portion 322 of the wall 320 to have a first thickness less than a second thickness of the second portion 324 of the wall 320.

In certain embodiments, providing at least a portion of the biocompatible housing 310 comprises providing a body 410 comprising the wall 320. FIGS. 6A and 6B schematically illustrate an example body 410 in accordance with certain embodiments described herein. The body 410 comprises one or more walls (including the wall 320) comprising a biocompatible material (e.g., titanium; titanium alloy), which generally surround at least a portion of an inner region 312 within the body 410. For clarity, in FIGS. 6A and 6B, the wall 320 is shown as shaded while the other walls are shown as unshaded.

The body 410 can include one or more openings 412 through one or more of the walls of the body 410. For example, the body 410 of FIG. 6A has an opening 412 on a wall 610 of the body 410 different from the wall 320 but adjacent to the wall 320 (e.g., sharing a corner with the wall 320; a top wall of the body 410), and the body 410 of FIG. 6B has an opening 412*a* on a wall 610 adjacent to the wall 320 and has an opening 412*b* on a wall 620 opposite to and non-adjacent to the wall 320 (e.g., not sharing a corner with the wall 320; a rear wall of the body 410). For example, the opening 412*b* through the wall 620 can be configured to be sealed by a corresponding plate or other structure comprising the at least one electrical feedthrough 420. In certain embodiments in which the body 410 has a smooth contour (e.g., no corner) between the wall 320 and any adjacent walls, the perimeter of the opening 412 is spaced sufficiently away from the first portion 324 of the wall 320 such that any joint seam subsequently formed while sealing (e.g., hermetically) the opening 412 does not affect the performance or vibrational characteristics of the diaphragm formed on the wall 320. While FIG. 6B shows the body 410 having two openings 412*a*, 412*b*, in certain other embodiments, the body 410 has only a single opening 412b through which access to the inner region 312 is provided during fabrication.

In certain embodiments, thinning the first portion 322 of the wall 320 comprises etching, mechanical machining, or electrical discharge machining the first portion 322 to remove material from a surface of the first portion 322 to reduce a thickness of the first portion 322 (e.g., such that the first portion 322 is sufficiently flexible to transmit vibrations between the outer region 311 and the inner region 312). In certain other embodiments, thinning the first portion 322 of the wall 320 comprises irradiating the first portion 322 with laser light 640 to remove material from a surface of the first portion 322 to reduce a thickness of the first portion 322 (e.g., laser micromachining) (e.g., such that the first portion 322 is sufficiently flexible to transmit vibrations between the outer region 311 and the inner region 312). For example, as schematically illustrated in FIG. 6A, an outer surface 630 of the first portion 322 of the wall 320 (e.g., facing an outer region 311 outside the body 410 or the housing 310) is irradiated with laser light 640 such that material is removed from the outer surface 630. For another example, as schematically illustrated in FIG. 6B, an inner surface 632 of the first portion 322 of the wall 320 (e.g., facing an inner region 312 bounded at least partially by the body 410 or within and bounded by the housing 310) is irradiated with laser light 640 such that material is removed from the surface of the inner side 632. As schematically illustrated in FIG. 6B, the laser light 640 can be directed through the opening 412 of the body 410 or housing 310 to impinge the inner surface 632 of the wall 320.

In certain embodiments, the laser light is generated by at least one laser (e.g., $CO_2$ laser; Nd laser; Nd:YAG laser; excimer laser; fiber laser) and is configured to controllably remove material (e.g., via ablation, vaporization, and/or melting) from a surface impinged by the laser light. For example, the laser light can be either continuous-wave (CW) or pulsed, and can comprise at least one wavelength (e.g., less than 20 microns; less than 10 microns; less than 1 micron; 10.6 microns for $CO_2$ laser; 1.064 microns for Nd:YAG laser), an average power (e.g., less than 100 W; less than 10 W; less than 1 W; less than 100 mW; less than 10 mW), a duty cycle (e.g., less than 50%; less than 20%; less than 10%), and a temporal pulse width (e.g., less than 1 millisecond; less than 100 microseconds; less than 10 microseconds; less than 1 microsecond; less than 100 nanoseconds; less than 10 nanoseconds; less than 1 nanosecond; less than 100 picoseconds; less than 10 picoseconds; less than 1 picosecond; less than 100 femtoseconds; less than 10 femtoseconds), and can have a spot size (e.g., less than 1 millimeter; less than 100 microns; less than 10 microns; less than 1 micron). In certain embodiments, one or both of the laser light 640 and the body 410 can be moved relative to one another to irradiate selected portions of the wall 320, thereby removing material from the first portion 322. For example, one or both of the laser and the body 410 can be mounted on a controllably-movable stage with a predetermined resolution of motion. In certain embodiments, thinning the first portion 322 of the wall 320 is performed while not thinning the second portion 324 of the wall 320 (e.g., only removing material from the first portion 322 and not removing material from the second portion 324).

In certain embodiments, the method 500 further comprises placing electronic circuitry 430 and a transducer 440 within the inner region 312, mechanically coupling the transducer 440 to the inner surface 632 of the wall 320, and mechanically coupling the elongate member 460 to the outer surface 630 of the wall 320. In certain embodiments, the method 500 further comprises hermetically sealing the opening 412 (e.g., after irradiating the inner surface 632 of the wall 320) by placing a lid 414 and/or plate over the opening 412 and joining (e.g., soldering; brazing; welding; laser welding) the lid 414 and/or plate to the body 410. For example, the plate can comprise the at least one electrical feedthrough 420, and the plate can be joined to the body 410 such that the at least one electrical feedthrough 420 is mechanically coupled to the housing 310 and extends between the inner region 312 and the outer region 311. The method 500 can further comprise mechanically coupling the at least one electrical feedthrough 420 to the electronic circuitry 430. In certain embodiments, thinning the first portion 322 of the wall 320 is performed before at least one of: mechanically coupling the transducer 440 to the inner surface 632 of the wall 320 and mechanically coupling the elongate member 460 to the outer surface 630 of the wall 320.

Certain embodiments described herein advantageously improve the fabrication of an implantable transducer assembly (e.g., implantable middle ear transducer assembly) by one or more of the following: reducing manufacturing time, reducing manufacturing overhead, reducing number of parts utilized, reducing cost of goods sold (COGS), avoiding expensive laser welding processes of the diaphragm, avoiding breaches of the housing to form the diaphragm. Certain embodiments described herein advantageously reduce the risk of hermeticity breaches of the implantable transducer assembly and/or damage during fabrication, thereby making the assembly more robust and cheaper to manufacture. Certain embodiments described herein advantageously provide a platform for implantable transducer assemblies by creating a generic housing comprises an integrated vibration port. Certain embodiments described herein can be advantageously applied to housings of any size or shape and can advantageously fabricate diaphragms of any size or shape, either by removing material from an outer surface of the housing and/or from an inner surface of the housing.

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. A method comprising:
providing a biocompatible housing configured to be implanted within a recipient, the housing comprising a plurality of wall portions comprising a first wall portion and other wall portions, the first wall portion and the other wall portions mechanically coupled to one another and at least partially bounding an inner region within the housing, the first wall portion comprising an inner surface facing the inner region within the housing; and while the first wall portion is mechanically coupled to the other wall portions, integrally forming a diaphragm on the first wall portion by thinning the first wall portion to have a first thickness less than a second thickness of a second wall portion of the other wall portions, wherein thinning the first wall portion comprises removing material from the inner surface of the first wall portion.

2. The method of claim 1, wherein thinning the first wall portion is performed while not thinning the second wall portion.

3. The method of claim 1, wherein thinning the first wall portion comprises irradiating the first wall portion with laser light to remove the material.

4. The method of claim 1, wherein thinning the first wall portion comprises etching, mechanical machining, or electrical discharge machining the first wall portion to remove the material.

5. The method of claim 1, wherein the first wall portion further comprises an outer surface facing an outer region outside the housing.

6. The method of claim 5, wherein thinning the first wall portion further comprises removing material from the outer surface of the first wall portion.

7. A method comprising:
providing at least a portion of a biocompatible housing configured to be implanted within a recipient, the portion comprising a wall; and
while a first portion of the wall is mechanically coupled to a second portion of the wall, integrally forming a diaphragm on the wall by thinning the first portion of the wall to have a first thickness less than a second thickness of the second portion of the wall, wherein thinning the first portion of the wall comprises removing material from an inner surface of the wall and removing the material from the inner surface of the wall comprises directing laser light through an opening of the housing to impinge the inner surface of the wall.

8. The method of claim 7, further comprising hermetically sealing the opening after irradiating the inner surface of the wall.

9. The method of claim 8, wherein hermetically sealing the opening comprises mechanically coupling at least one electrical feedthrough to the housing.

10. The method of claim 8, wherein hermetically sealing the opening comprises mechanically coupling at least one lid to the housing.

11. The method of claim 7, wherein, after said thinning the first portion of the wall, the first portion has a thickness between an inner side of the first portion and an outer side of the first portion in a range of 10 microns to 100 microns.

12. The method of claim 7, wherein the housing comprises a first opening, and the method further comprises hermetically sealing the first opening by joining an electrical feedthrough to the housing.

13. The method of claim 12, wherein the housing comprises a second opening, and the method further comprises hermetically sealing the second opening by joining a biocompatible lid to the housing.

14. A method comprising:
providing a biocompatible housing configured to be implanted within a recipient, the housing comprising a plurality of wall portions comprising a first wall portion and other wall portions, the first wall portion and the other wall portions mechanically coupled to one another and at least partially bounding an inner region within the housing; and
while the first wall portion is mechanically coupled to the other wall portions, integrally forming a diaphragm on the first wall portion by thinning the first wall portion to have a first thickness less than a second thickness of a second wall portion of the other wall portions, wherein the housing comprises a planar and unitary wall comprising the first wall portion and the second wall portion and, after said thinning the first wall portion, the first wall portion is sufficiently flexible to transmit vibrations between an outer region outside the housing and the inner region.

15. The method of claim 14, wherein the first wall portion and the second wall portion are in mechanical communication with one another without a joint seam between the first wall portion and the second wall portion.

16. The method of claim 14, wherein the inner region is configured to contain a transducer in mechanical communication with the first wall portion, the housing bounding the inner region and hermetically sealing the inner region from the outer region.

17. A method comprising:
providing a biocompatible housing configured to be implanted within a recipient, the housing comprising a plurality of wall portions comprising a first wall portion and other wall portions, the first wall portion and the other wall portions mechanically coupled to one another and at least partially bounding an inner region within the housing, the inner region configured to contain a transducer in mechanical communication with the first wall portion, the housing configured to bound the inner region and to hermetically seal the inner region from an outer region outside the housing; and
while the first wall portion is mechanically coupled to the other wall portions, integrally forming a diaphragm on the first wall portion by thinning the first wall portion to have a first thickness less than a second thickness of a second wall portion of the other wall portions, wherein the housing comprises a unitary wall comprising the first wall portion and the second wall portion and, after said thinning the first wall portion, the first wall portion is sufficiently flexible to transmit vibrations between the outer region and the inner region, wherein the housing further comprises at least one electrical feedthrough in electrical communication with the transducer and configured to transmit electrical signals between the inner region and the outer region.

18. The method of claim 17, wherein the transducer is configured to generate the vibrations in response to electrical signals.

19. The method of claim 17, wherein the transducer is configured to receive the vibrations and to generate electrical signals indicative of the vibrations.

20. The method of claim 17, wherein the housing comprises an opening and the at least one electrical feedthrough extends through a plate configured to be joined to the housing to hermetically seal the opening.

* * * * *